US007723398B2

(12) United States Patent
Ilg et al.

(10) Patent No.: US 7,723,398 B2
(45) Date of Patent: May 25, 2010

(54) IN-CAN STABILIZER BLEND

(75) Inventors: Stephan Ilg, Giebenach (CH); Edith Pighetti, Binningen (CH); Peter Nesvadba, Marly (CH); André Fuchs, Schliengen-Obereggenen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 11/918,694

(22) PCT Filed: Apr. 12, 2006

(86) PCT No.: PCT/EP2006/061535

§ 371 (c)(1),
(2), (4) Date: Jan. 16, 2009

(87) PCT Pub. No.: WO2006/111494

PCT Pub. Date: Oct. 26, 2006

(65) Prior Publication Data

US 2009/0176906 A1 Jul. 9, 2009

(30) Foreign Application Priority Data

Apr. 21, 2005 (EP) ................... 05103228

(51) Int. Cl.
*C08F 2/50* (2006.01)
*C08J 3/28* (2006.01)
*C08K 5/04* (2006.01)
*C08K 5/15* (2006.01)
*C08K 5/16* (2006.01)

(52) U.S. Cl. ............... 522/78; 522/71; 522/6; 522/74; 522/75; 522/81; 522/90; 522/104; 522/100; 522/170; 522/168; 522/150; 522/151; 522/152; 522/153; 522/173; 522/174; 522/178; 522/179; 524/80; 524/81; 524/86; 524/87; 524/92; 524/94; 524/95; 524/96; 524/97; 524/99; 524/102; 524/104; 524/105; 106/31.13; 106/31.6

(58) Field of Classification Search .............. 522/71, 522/74, 75, 78, 6, 81, 90, 104, 100, 170, 522/168, 150, 151, 152, 153, 173, 174, 178, 522/179; 524/80, 81, 86, 87, 92, 94, 95, 524/96, 97, 99, 102, 104, 105; 106/31.13, 106/31.6

See application file for complete search history.

(56) References Cited

U.S. PATENT DOCUMENTS

| 5,616,774 | A  | * | 4/1997 | Evans et al. ............ 252/182.18 |
| 5,912,106 | A  | * | 6/1999 | Chang et al. ............. 430/281.1 |
| 6,926,820 | B2 | * | 8/2005 | Eldin et al. ............. 208/48 AA |
| 7,045,647 | B2 | * | 5/2006 | Benage ...................... 560/4 |
| 7,084,196 | B2 | * | 8/2006 | Troutman et al. ............ 524/94 |
| 7,473,795 | B2 | * | 1/2009 | Benage ...................... 560/4 |
| 2003/0073762 | A1 |   | 4/2003 | Jung et al. ................... 524/99 |
| 2004/0010159 | A1 | * | 1/2004 | Benage ...................... 558/306 |
| 2005/0192384 | A1 |   | 9/2005 | Jung et al. ................... 524/99 |
| 2006/0155140 | A1 | * | 7/2006 | Benage ...................... 560/4 |
| 2007/0225397 | A1 | * | 9/2007 | Nasvadba et al. .......... 522/167 |

* cited by examiner

*Primary Examiner*—Sanza L McClendon
(74) *Attorney, Agent, or Firm*—Joseph C. Suhadolnik

(57) ABSTRACT

The invention relates to a radiation curable coating or an ink composition comprising a photoinitiator and a stabilizer blend of a sterically hindered nitroxyl radical and a quinone methide.

4 Claims, No Drawings

IN-CAN STABILIZER BLEND

The present invention relates to the stabilisation of radiation curable coating compositions and inks (In-can stabilization) against premature polymerisation or crosslinking during transportation and storage and to the use of a stabilizer blend as In-Can stabilizer for radiation curable coatings and inks.

Radiation-curable inks and coatings have been one of the fastest growing technologies in the past two decades. This growth is forecast to continue well into the future with the development of new applications for radiation curing, such as inks for food packaging. New raw materials are required to ensure that radiation-technology can meet the challenging demands of low odour and low migration, low yellowing while maintaining high reactivity.

Especially UV-curable inks and coatings are sensitized by the photoinitiator and thus have to be stabilised against undesired polymerisation or crosslinking in order that they have adequate storage stability without reducing the cure-speed when radiated. The stabilizers should be compatible with a wide range of commercially available oligomers.

In the prior art, for example in US2003/073762 or EP1235863, there are proposed for that purpose sterically hindered nitroxyl radicals in general. Examples of typical radical scavenger that prevent the gelation of UV curable compositions while having minimal impact on curing speed are bis(1-oxy-2,2,6,6-tetramethylpiperidin-4-yl)sebacate (Irgastab® UV 10) and 4-hydroxy-1-oxy-2,2,6,6-tetramethylpiperidine.

US2004/010159 describes a method for inhibiting the premature polymerization of ethylenically unsaturated monomers comprising adding to said monomers an effective amount of: A) at least one nitroxyl compound, and B) at least one quinone alkide compound having an electron-withdrawing group at the 7-position. Additionally, a composition is disclosed that comprises: A) at least one nitroxyl compound, and B) at least one quinone alkide compound having an electron-withdrawing group at the 7-position. The composition is not dedicated to radiation curable coating or ink composition containing photoinitiators.

EP 0 737 660 B1 (Nalco) describes a process for reducing premature polymerization of readily polymerizable unsaturated monomers during monomer manufacturing processes by incorporating therein an effective amount of a 7-aryl quinone methide compound. Also disclosed is the stabilization by a blend of 7-aryl quinone methide compounds and stable nitroxyl compounds.

The International Publication WO01/40404 describes the inhibition of the polymerization of ethylenically unsaturated monomers by means of the addition thereto of hydrogen donors and/or electron acceptors, either alone or in combination with at least one stable nitroxide free radical compound. The electron acceptor may be a quinone methide.

The problem underlying the present invention is therefore to provide stabilisers, which are effective radical scavenger that prevent the degradation of radiation curable compositions (inks and coatings), while having minimal impact on curing speed. The stabilizers should be especially suitable in pigmented systems. Some pigments, for instance orange, green and black pigments, are known to have a negative influence on the storage stability. A specific problem occurs when Orange 34 is used.

It has now been found that this problem is solved by adding to the inks and coatings a blend of a sterically hindered nitroxyl radical with a quinone methide.

Thus, the invention relates to a radiation curable coating- or ink composition comprising a) a photoinitiator;
b) a stabilizer blend of a sterically hindered nitroxyl radical and a quinone methide.

Furthermore, the invention relates to a method for increasing the storage stability of a radiation curable coating composition or ink composition by adding to the coating- or the ink composition, optionally comprising a photoinitiator, a stabilizer blend of a sterically hindered nitroxyl radical and a quinone methide. Radiation is electromagnetic radiation, such as near infrared (NIR), visible light, UV radiation or X-radiation, especially UV radiation, and corpuscular radiation such as electron beams.

Thus, the stabilizer blend also increases the storage stability of a coating or ink composition which does not contain a photoinitiator.

The storage stabilisation of resins not containing a photoinitiator is especially important if a reactive binder such as an amine acrylate is present.

Furthermore, the invention relates to the use of a stabilizer blend of a sterically hindered nitroxyl radical and a quinone methide as IN-CAN stabilizer for coating or ink compositions which optionally contain a photoinitiator.

The mol ratio of the sterically hindered nitroxyl radical to the quinone methide is from 1 to 99 mol % to 99 to 1 mol %, preferably 120 mol % to 99-80 mol %.

In an especially preferred blend the sterically hindered nitroxyl radical and the quinone methide are present as an eutectic mixture (10 mol % of the sterically hindered nitroxyl radical and 90 mol % of the quinone methide).

The blend is added in an amount of from 0.0001 to 10% by weight, based on the total amount of coating composition or ink composition, preferably 0.01 to 5%.

Sterically hindered nitroxyl compounds are those as disclosed in EP 1235863

The stable sterically hindered nitroxyl free-radicals have the following formula,

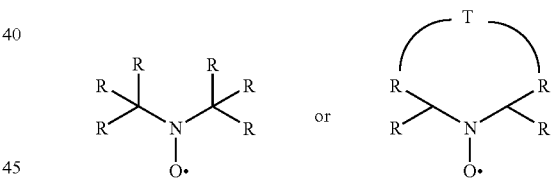

wherein R is alkyl and T is a group required to complete a 5- or 6-membered ring. R is preferably $C_1$-$C_4$alkyl, especially methyl, when it is a cyclic nitroxyl free-radical.

Two or more nitroxyl groups in the same molecule can be linked to one another by way of the group T, as shown below. E has the meaning of a spacer group such as for example a $C_1$-$C_{12}$alkylene group.

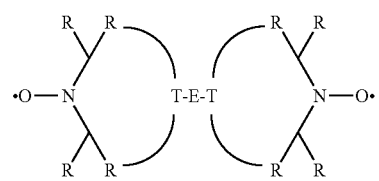

Typical nitroxyl free-radicals are, for example:
bis(1-oxy-2,2,6,6-tetramethylpiperidin-4-yl) sebacate, 4-hydroxy-1-oxy-2,2,6,6-tetramethylpiperidine, 4-ethoxy-1- oxy-2,2,6,6-tetramethylpiperidine, 4-propoxy-1-oxy-2,2,6, 6-tetramethylpiperidine, 4-acetamido-1-oxy-2,2,6,6-tetramethylpiperidine, 1-oxy-2,2,6,6-tetramethylpiperidine, 1-oxy-2,2,6,6-tetramethylpiperidin-4-one, 1-oxy-2,2,6,6-tetramethylpiperidin-4-yl acetate, 1-oxy-2,2,6,6-tetramethylpiperidin-4-yl 2-ethylhexanoate, 1-oxy-2,2,6,6-tetramethylpiperidin-4-yl stearate, 1-oxy-2,2,6,6-tetramethylpiperidin-4-yl benzoate, 1-oxy-2,2,6,6-tetramethylpiperidin-4-yl 4-tert-butyl-benzoate, bis(1-oxy-2, 2,6,6-tetramethylpiperidin-4-yl) succinate, bis(1-oxy-2,2,6, 6-tetramethylpiperidin-4-yl)adipate, bis(1-oxy-2,2,6,6-tetramethylpiperidin-4-yl)n-butylmalonate, bis(1-oxy-2,2,6, 6-tetramethylpiperidin-4-yl)phthalate, bis(1-oxy-2,2,6,6-tetramethylpiperidin-4-yl)isophthalate, bis(1-oxy-2,2,6,6-tetramethylpiperidin-4-yl)terephthalate, bis(1-oxy-2,2,6,6-tetramethylpiperidin-4-yl)hexahydroterephthalate, N,N'-bis (1-oxy-2,2,6,6-tetramethylpiperidin-4-yl)adipamide, N-(1-oxy-2,2,6,6-tetramethylpiperidin-4-yl)caprolactam, N-(1-oxy-2,2,6,6-tetramethylpiperidin-4-yl)dodecylsuccinimide, 2,4,6-tris[N-butyl-N-(1-oxy-2,2,6,6-tetramethylpiperidin-4-yl)]-s-triazine, 4,4'-ethylenebis(1-oxy-2,2,6,6-tetramethylpiperazin-3-one), 2-oxy-1,1,3,3-tetramethyl-2-isobenzazole, 1-oxy-2,2,5,5-tetramethylpyrrolidine and N,N-bis(1,1, 3,3-tetramethylbutyl)nitroxide.

Preferred nitroxyl free-radicals are: bis(1-oxy-2,2,6,6-tetramethylpiperidin-4-yl)sebacate, 4-hydroxy-1-oxy-2,2,6,6-tetramethylpiperidine, 4-ethoxy-1-oxy-2,2,6,6-tetramethylpiperidine, 4-propoxy-1-oxy-2,2,6,6-tetramethylpiperidine, 4-acetamido-1-oxy-2,2,6,6-tetramethylpiperidine, 1-oxy-2,2,6,6-tetramethylpiperidine and 1-oxy-2,2,6,6-tetramethylpiperidin-4-one.

Bis(1-oxy-2,2,6,6-tetramethylpiperidin-4-yl)sebacate and 4-hydroxy-1-oxy-2,2,6,6-tetramethylpiperidine are especially preferred.

The nitroxyl radicals are commercially available or can be prepared according to known methods, for example as described in Ciba U.S. Pat. No. 4,665,185.

Commercially available is, for example, Ciba® IRGASTAB® UV10. Bis(1-oxy-2,2,6,6-tetramethylpiperidin-4-yl)sebacate.

Quinone methides are those of the formula

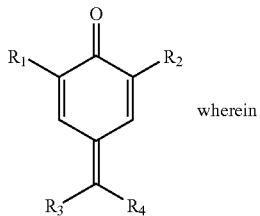

wherein $R_1$ and $R_2$ independently of each other are $C_1$-$C_{18}$alkyl, $C_5$-$C_{12}$cycloalkyl, $C_7$-$C_{15}$-phenylalkyl, optionally substituted $C_6$-$C_{10}$ aryl;

$R_3$ and $R_4$ independently of each other are H, optionally substituted $C_6$-$C_{10}$-aryl, 2-,3-,4-pyridyl, 2-,3-furyl or thienyl, COOH, COOR$_{10}$, CONH$_2$, CONHR$_{10}$, CONR$_{10}$R$_{11}$, —CN, —COR$_{10}$, —OCOR$_{10}$, —OPO(OR$_{10}$)$_2$, wherein $R_{10}$ is $C_1$-$C_8$alkyl or phenyl.

Preferably $R_1$ and $R_2$ are tert. butyl. $R_3$ is preferably H. $R_4$ is preferably COOR$_{10}$, phenyl or CN, more preferably phenyl.

Examples are 4-benzylidene-2,6-di-tert!-butyl-cyclohexa-2,5-dienone and (3,5-Di-tert!-butyl-4-oxo-cyclohexa-2,5-dienylidene)-acetonitrile.

Quinone methides can be prepared according to known methods, for example as described in Ciba Patent EP 744392 which describes a process for the preparation of 7-aryl-2,6-disubstituted quinone methides U.S. Pat. No. 4,032,547 describes an oxidation process for the preparation of quinone methides from hindered phenols using ferricyanide as the secondary oxidant in combination with persulfate as the primary oxidant.

German DEOS 2,734,239 discloses a process for the preparation of 2,6-di-tert-alkyl-4-alkylidene-2,5-cyclohexadienones by treatment of bis(3,5-di-tert-alkyl-4-hydroxybenzyl) sulfides with alkaline heavy metal compounds.

B. Koutek et al., Synthetic Communications, 6 (4), 305 (1976) describe a method for the preparation of 4-alkylidene-2,5-cyclohexadien-1-ones by the facile cleavage of 4-hydroxybenzyl sulfonates with aqueous alkali. The sulfonates are prepared from the corresponding 4-hydroxybenzyl alcohols.

By the term "in can stabilizer" is meant a stabilizer that improves the long term storage stability.

The term "coating composition" is used to describe any composition which is applied to a substrate surface and cured by free radical polymerization optionally in the presence of a photoinitiator and optionally in addition in the presence a thermal initiator.

The coating composition may be a pigmented or unpigmented urethane resins, acrylic resins, polyester resins, and epoxy resins.

Such composition may be aqueous or non-aqueous and may contain pre-polymerized polymers or polymerizable monomers, oligomers and/or polymers and optionally other additives including a surfactant and/or emulsifier and a solvent, among numerous other additives.

The coating is a radiation curable coating, preferably an UV curable coating composition or a double-(thermal and UV radiation) curable coating composition. The thermal curing is carried out using NIR-curing or IR-curing or convection heat. The double curing composition comprises in addition to the photoinitiator a thermal initiator. The double curing is carried out using NIR-curing or IR-curing followed by UV-curing or vice versa.

The coating composition comprises at least an ethylenically unsaturated compound which may be a monomer, an oligomer or a prepolymer, a blend thereof or a copolymer thereof.

Ethylenically unsaturated polymerizable monomers are selected from the group consisting of (meth)acrylates, alkenes, conjugated dienes, styrenes, acrolein, vinyl acetate, vinyl-pyrrolidone, vinylimidazole, maleic anhydride, fumaric anhydride, (meth)acrylic acid, (meth)acrylic acid derivatives such as esters and amides, vinyl halides and vinylidene halides. Preferred are compounds having (meth)acryloyl, vinyl and/or maleinate groups. Especially preferred are (meth)acrylates.

Compounds which contain free-radically polymerizable double bonds in the form of the preferred (meth)acryloyl groups may be produced in accordance with conventional methods. This may proceed, for example, by transesterifying OH-functional resins, such as OH-functional polyesters, polyacrylates, polyurethanes, polyethers or epoxy resins, with alkyl esters of (meth)acrylic acid; esterifying the stated OH-functional resins with (meth)acrylic acid; reacting the stated OH-functional resins with isocyanate-functional (meth)acrylates; reacting acid-functional resins, such as polyesters, polyacrylates, polyurethanes with epoxy-functional (meth)acrylates; reacting epoxy-functional resins, such as polyesters, poly-acrylates, epoxy resins with (meth)acrylic acid. These production methods stated by way of example are described in the literature and known to the person skilled in the art.

Examples of prepolymers or oligomers include (meth)acryloyl-functional (meth)acrylic copolymers, polyurethane (meth)acrylates, polyester (meth)acrylates, unsaturated polyesters, polyether (meth)acrylates, silicone (meth)acrylates and epoxy resin (meth)acrylates, amine(meth)acrylates, dialkylamino alkyl(meth)acrylates (e.g., diethylaminoethylacrylate) or N-morpholinoalkyl-(meth)acrylates (e.g., N-morpholinoethyl-acrylate) having number-average molecular masses from, for example, 500 to 10,000, preferably 500 to 5,000.

The (meth)acryloyl-functional prepolymers may be used in combination with reactive diluents, i.e., free-radically polymerizable low molecular weight compounds with a molar mass of below 500 g/mol. The reactive diluents may be mono-, di- or polyunsaturated. Examples of monounsaturated reactive diluents are (meth)acrylic acid and the esters thereof, maleic acid and the esters thereof, vinyl acetate, vinyl ether, substituted vinyl ureas, styrene, vinyltoluene. Examples of diunsaturated reactive diluents are di(meth)acrylates such as alkylene glycol di(meth)acrylate, polyethylene glycol di(meth)acrylate, 1,3-butanediol di-(meth)acrylate, vinyl(meth)acrylate, allyl(meth)acrylate, divinylbenzene, dipropylene glycol di(meth)acrylate, hexanediol di(meth)acrylate. Examples of polyunsaturated reactive diluents are glycerol tri(meth)acrylate, trimethylolpropane tri(meth)acrylate, pentaerythritol tri(meth)-acrylate, pentaerythritol tetra(meth)acrylate. The reactive diluents may be used alone or in blend.

Suitable salts of acrylic acid or methacrylic acid are, for example, $(C_1-C_4alkyl)_4$ammonium or $(C_1-C_4alkyl)_3NH$ salts, e.g. the tetramethylammonium, tetraethylammonium, trimethylammonium or triethylammonium salt, the trimethyl-2-hydroxyethylammonium or triethyl-2-hydroxyethylammonium salt, the dimethyl-2-hydroxyethylammonium or diethyl-2-hydroxyethylammonium salt.

The ethylenically unsaturated compounds may contain, in addition to the olefinic double bonds, one or more further, identical or different functional groups. Examples of functional groups include hydroxyl, isocyanate (optionally blocked), N-methylol, N-methylolether, ester, carbamate, epoxy, amino (optionally blocked), acetoacetyl, alkoxysilyl and carboxyl groups. Examples are polyurethane resins with (meth)acryloyl groups and glycerol mono- and di(meth)acrylate, trimethylol propane mono- and di(meth)acrylate or pentaerythritol tri(meth)acrylate.

Thermal curing refers to the application of convection heat or IR- or NIR-radiation after the blend has been applied to substrate. In case of powder coatings the adhered powder coating is first melted to form a surface layer preferably by convection heat. Suitable temperatures to initiate and complete free-radical polymerization are 60-180° C.

NIR-curing

The NIR radiation used in the process according to the invention is short-wave infrared radiation in the wavelength range from about 750 nm to about 1500 nm, preferably 750 nm to 1200 nm. Radiation sources for NIR radiation include, for example, conventional NIR radiation emitters, which are available commercially (for example, from Adphos).

IR-curing

The IR radiation used in the process according to the invention is medium wave radiation in the wave length range from about 1500 nm to about 3000 nm and/or longer-wave infrared radiation in the wave length range above 3000 nm.

IR radiation emitters of this kind are available commercially (for example, from Heraeus).

UV-curing

The photochemical curing step is carried out usually using light of wavelengths from about 200 nm to about 600 nm, especially from 200 to 450 nm. As light sources there are used a large number of the most varied types. Both point sources and planiform projectors (lamp carpets) are suitable. Examples are: carbon arc lamps, xenon arc lamps, medium-, high- and low-pressure mercury lamps, optionally doped with metal halides (metal halide lamps), microwave-excited metal-vapor lamps, excimer lamps, super actinic fluorescent tubes, fluorescent lamps, argon filament lamps, electronic flash lamps, photographic flood lights, electron beams and X-rays generated by means of synchrotrons or laser plasma.

Double curable systems comprise ethylenically unsaturated monomers, which can be polymerized by UV radiation or which can be polymerized thermally induced by IR or NIR radiation or by convection heat. In a double cure system the thermal curing is preferably followed by UV-curing. However, it is also possible that the UV-curing follows the thermal curing.

Dual curable systems comprise ethylenically unsaturated monomers, which can be polymerized thermally induced by IR or NIR radiation or by convection heat. Furthermore, at least one second thermal crosslinkable compound is present. The second compound preferably crosslinks via a polyol-isocyanate reaction to form a polyurethane.

Electron beam curing is conducted using an electron beam chamber which provides a large area electron source. Electron beam chambers are commercially available.

UV curable coatings containing a photoinitiator are preferred.

The coating composition may also be an ink composition. Thus, the substrate is printed with an ink composition to form an ink film on the substrate.

Non limiting examples for radiation curable inks are: inks for printing processes, for flexographic printing, screen printing, packaging printing, security ink printing, intaglio printing or offset printing, for pre-press stages and for textile printing, for office, home applications or graphics applications, such as for paper goods, for example, for ballpoint pens, felt tips, fiber tips, card, wood, (wood) stains, metal, inking pads or inks for impact printing processes (with impact-pressure ink ribbons), for the preparation of non-impact-printing material for digital printing, for the thermal wax transfer printing process, the ink jet printing process or for the thermal transfer printing process, and also for the preparation of polymeric ink particles, toners, dye lasers, dry copy toners liquid copy toners, or electrophotographic toners, and electroluminescent devices.

Preferred are offset inks, flexographic inks, screen inks and ink jet inks.

Additives

The above-described compositions may further comprise customary additives, which may, as an alternative, also be added after the polymerization. Such additives can be added in small amounts, e.g. UV-absorbers or light stabilizers, e.g. compounds selected from the group consisting of hydroxyphenylbenzotriazoles, hydroxyphenylbenzophenones, oxalamides and hydroxyphenyl-s-triazines. Particularly suitable light stabilizers are those selected from the group consisting of N-alkoxy-Hals compounds such as Tinuvin 123, or of sterically hindered amines Hals compounds of the 2-(2-hydroxyphenyl)-1,3,5-triazine or 2-hydroxyphenyl-2H-benzotriazole type. Examples of light stabilizers of the 2-(2- hydroxyphenyl)-1,3,5-triazine type are known from the patent literature, e.g. U.S. Pat. No. 4,619,956, EP-A-434 608, U.S. Pat. No. 5,198,498, U.S. Pat. No. 5,322,868, U.S. Pat. No. 5,369,140, U.S. Pat. No. 5,298,067, WO-94/18278, EP-A-704 437, GB-A-2,297,091 or WO-96/28431. 3,3,5,5 polysubstituted morpholin-2-one derivatives as described in U.S. Pat. No. 6,140,326 are well established light stabilizers for coatings.

The compositions may further comprise other customary additives such as leveling agents, rheology-influencing agents, such as, fine-particle silicic acid, layer silicates, urea compounds; thickeners, e.g., based on partially cross-linked carboxy-functional polymers or polyurethanes; defoamers, wetting agents, anti-crater agents, degassing agents, e.g., benzoin, antioxidants.

Suitable photoinitiators are known to those skilled in the art.

For example, α-hydroxyketones and α-aminoketones, phenylglyoxalates or phospinoxides are photoinitiators commonly used in graphic arts applications.

Especially preferred are, for example, the following commercially available photoinitiators:

DAROCUR 1173: 2-hydroxy-2-methyl-1-phenyl-1-propanone (HMPP) and Oligomeric HMPP,
IRGACURE 184: 1-hydroxy-cyclohexyl-phenylketone,
IRGACURE 2959: 2-hydroxy-1-[4-(2-hydroxyethoxy)phenyl]-2-methyl-1-propanone,
IRGACURE 369: 2-benzyl-2-(dimethylamino)-1-[4-(4-morpholinyl)phenyl]-1-butanone,
IRGACURE 1300: Irgacure 369+Irgacure 651 (benzildimethylketal),
IRGACURE 379: 2-(4-Methylbenzyl)-2-(dimethylamino)-1-[4-(4-morpholinyl)phenyl]-1-butanone,
IRGACURE 127: 2-Hydroxy-1-{4-[4-(2-hydroxy-2-methyl-propionyl)-benzyl]-phenyl}-2-methyl-propan-1-one,
IRGACURE 754: oxo-phenyl-acetic acid 1-methyl-2-[2-(2-oxo-2-phenyl-acetoxy)-propoxy]-ethyl ester,
IRGACURE 819: bis(2,4,6-trimethylbenzoyl)-phenylphosphine oxide,
IRGACURE 2100: a blend of Irgacure 819 and Lucerin TPO (2,4,6-Trimethylbenzoyl-phenyl phosphinic acid ethyl ester),
IRGACURE 2022: a blend of Irgacure 819 and Lucerin TPO and Darocur 1173,
IRGACURE 250: 4-isobutylphenyl-4-methylphenyl iodonium hexafluorophosphate,
DAROCUR ITX: 2-isopropylthioxanthone and 4-isopropylthioxanthone,
DAROCUR EDB: ethyl-4-dimethylamino benzoate,
DAROCUR EHA: 2-ethylhexyl-4-dimethylamino benzoate.

The above examples of photoinitiators are not limiting.

Any thermal initiator known in the art may be used. For example the thermal initiators are peroxides such as dialkyl peroxides, dicumyl peroxide, peroxo carboxylic acids and so one and azo initiators as disclosed in U.S. Pat. No. 5,922,473.

Pigments which may be used in pigmented coatings and inks include organic and inorganic pigments, alone or in combination. The exact choice of pigments will depend upon the specific application and performance requirements such as color reproduction and image stability. Pigments suitable for use in the present invention include, for example, azo pigments, monoazo pigments, disazo pigments, azo pigment lakes, beta-Naphthol pigments, Naphthol AS pigments, benzimidazolone pigments, disazo condensation pigments, metal complex pigments, isoindolinone and isoindoline pigments, polycyclic pigments, phthalocyanine pigments, quinacridone pigments, perylene and perinone pigments, thioindigo pigments, anthrapyrimidone pigments, flavanthrone pigments, anthanthrone pigments, dioxazine pigments, triarylcarbonium pigments, quinophthalone pigments, diketopyrrolo pyrrole pigments, titanium oxide, iron oxide, and carbon black. Typical examples of pigments which may be used include Color Index (C.I.) Pigment Yellow 1, 2, 3, 5, 6, 10, 12, 13, 14, 16, 17, 62, 65, 73, 74, 75, 81, 83, 87, 90, 93, 94, 95, 97, 98, 99, 100, 101, 104, 106, 108, 109, 110, 111, 113, 114, 116, 117, 120, 121, 123, 124, 126, 127, 128, 129, 130, 133, 136, 138, 139, 147, 148, 150, 151, 152, 153, 154, 155, 165, 166, 167, 168, 169, 170, 171, 172, 173, 174, 175, 176, 177, 179, 180, 181, 182, 183, 184, 185, 187, 188, 190, 191, 192, 193, 194; C.I. Pigment Orange 1, 2, 5, 6, 13, 15, 16, 17, 17:1, 19, 22, 24, 31, 34, 36, 38, 40, 43, 44, 46, 48, 49, 51, 59, 60, 61, 62, 64, 65, 66, 67, 68, 69; C.I. Pigment Red 1, 2, 3, 4, 5, 6, 7, 8, 9, 10, 11, 12, 13, 14, 15, 16, 17, 18, 21, 22, 23, 31, 32, 38, 48:1, 48:2, 48:3, 48:4, 49:1, 49:2, 49:3, 50:1, 51, 52:1, 52:2, 53:1, 57:1, 60:1, 63:1, 66, 67, 68, 81, 95, 112, 114, 119, 122, 136, 144, 146, 147, 148, 149, 150, 151, 164, 166, 168, 169, 170, 171, 172, 175, 176, 177, 178, 179, 181, 184, 185, 187, 188, 190, 192, 194, 200, 202, 204, 206, 207, 210, 211, 212, 213, 214, 216, 220, 222, 237, 238, 239, 240, 242, 243, 245, 247, 248, 251, 252, 253, 254, 255, 256, 258, 261, 264; C.I. Pigment Violet 1, 2, 3, 5:1, 13, 19, 23, 25, 27, 29, 31, 32, 37, 39, 42, 44, 50; C.I. Pigment Blue 1, 2, 9, 10, 14, 15:1, 15:2, 15:3, 15:4, 15:6, 15, 16, 18, 19, 24:1, 25, 56, 60, 61, 62, 63, 64, 66; C.I. Pigment Green 1, 2, 4, 7, 8, 10, 36, 45; C.I. Pigment Black 1, 7, 20, 31, 32, and C.I. Pigment Brown 1, 5, 22, 23, 25, 38, 41, 42. In a preferred embodiment of the invention, the pigment employed is C.I. Pigment Blue 15:3, C.I. Pigment Red 122, C.I. Pigment Yellow 155, C.I. Pigment Yellow 74, bis(phthalocyanylalumino)tetraphenyldisiloxane or C.I. Pigment Black 7.

APPLICATION EXAMPLES

Three technical parameters of the new stabilizers were tested:
1. Stabilization efficiency at 70° C.
   a) in TMPTA (Trimethylolpropane triacrylate) which contains 5% photoinitiator IRGACURE 369 (2-benzyl-2-(dimethylamino)-1-[4-(4-morpholinyl)phenyl]-1-butanone)
   b) in UV-curable offset ink, which contains Pigment Orange 34.
2. Influence of the presence of the new In-can stabilizer on the curing efficiency of blue UV-curable offset ink.
3. Influence of the presence of the new In-can stabilizer on Yellowing.

Experimental Details

Preparation of the Eutectic Blend 20 parts of an eutectic blend of bis(1-oxyl-2,2,6,6-tetramethylpiperidin-4-yl)sebacate and 4-benzylidene-2,6-ditert.butyl-cyclohexa-2,5-dienone (17/83 g/g; 10/90 Mol/Mol) is dissolved in 80 part of OTA 480 (oligomer triacrylate, UCB)

The solubility in OTA 480 is as follows:

| Product A (bis(1-oxyl-2,2,6,6-tetramethylpiperidin-4-yl)sebacate) | 2-3% |
|---|---|
| Product B 4-benzylidene-2,6-ditert.butyl-cyclohexa-2,5-dienone) | 20% |
| Eutectic mixture A/B | 20%. |

It is also possible to melt bis(1-oxyl-2,2,6,6-tetramethylpiperidin-4-yl)sebacate and 4-benzylidene-2,6-ditert.butyl-cyclohexa-2,5-dienone (17/83 gIg; 10/90 Mol/Mol) together.

Storage Stability of TMPTA 5 g IRGACURE 369 (2-Benzyl-2-(dimethylamino)-1-[4-(4-morpholinyl)phenyl]-1-butanone) were added to 95 g TMPTA (Trimethylolpropane triacrylate monomer, UCB) and stirred to give a clear, yellowish solution with an initiator concentration of 5 wt-%. 0.1 g stabilizer were added to the solution and stirred until the substance was dissolved completely. 2 ml of the solutions were filled into 2.5 ml-analytical vials and placed in a drying oven (2 samples per substance and concentration). The samples were stored at 70° C. and the polymerization (usually starting at the bottom, to the top) was checked visually (reported as days until the polymerization started).

The results are as follows:

| Stabilizer | Starting point of polymerization Days at 70° C. |
|---|---|
| 0.1% Stabilizer A | 18 |
| 0.1% Stabilizer B | 5 |
| 0.1% Eutectic Blend A/B = 1/9 Mol/Mol, 0.5% solution | 23 |
| 0.1% Eutectic Blend A/B = 1/9 Mol/Mol, 0.5% solution in diethanolamin | >27 |

A

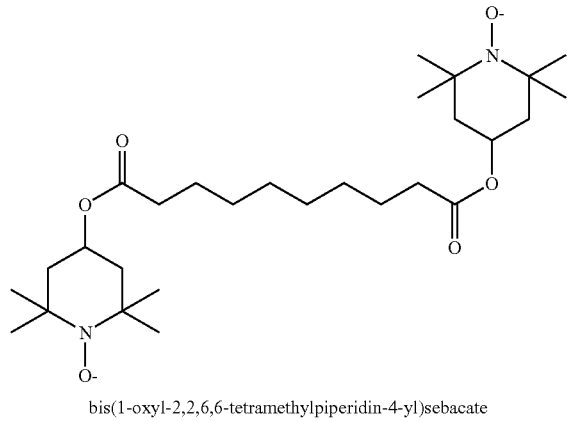

bis(1-oxyl-2,2,6,6-tetramethylpiperidin-4-yl)sebacate

B

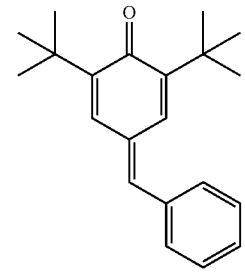

4-benzylidene-2,6-di-tert.butyl-cyclohexa-2,5-dienone

Storage Stability of Orange Offset Ink 0.2 g of a TMPTA (Trimethylolpropane triacrylate monomer, UCB) solution containing 2.5 wt-% stabilizer were added to 5.0 g of a commercial orange offset ink (Orange SICPA Pol without stabilizer) and were distributed homogeneously. 2.4 g of the ink were filled into a weighing container (glass, diameter 13 mm) and placed in a drying oven. The samples were stored at 70° C. and the polymerization of the ink (usually starting at the bottom, to the top) was checked with a spatula (reported as days until the polymerization started).

The results are as follows:

| Stabilizer | Starting point of polymerization Days at 70° C. |
|---|---|
| 0.1% Stabilizer A | 4 |
| 0.1% Stabilizer B | 25 |
| 0.1% Eutectic Blend A/B = 1/9 Mol/Mol, 0.5% solution | 25 |
| 0.1% Eutectic Blend A/B = 1/9 Mol/Mol, 0.5% solution in diethanolamin | 25 |

Influence of the Stabilizer on the Curing Efficiency of a Blue Offset Ink

For the assessment of the influence on curing efficiency, a blue UV offset ink was selected as appropriate testing system.

Composition of the Blue Offset Ink:

| Weight (g) | Raw material | Remark |
|---|---|---|
| 18.3 | EBECRYL 1608 (UCB) | Diluted epoxyacrylate in GPTA |
| 18.3 | EBECRYL 657 (UCB) | Polyester tetraacrylate |
| 20.0 | EBECRYL 220 (UCB) | Aromatic urethane hexaacrylate |
| 20.9 | EBECRYL 150 (UCB) | Diluting epoxyacrylate |
| 22.5 | IRGALITE Blue GLO (Ciba) | Copper phthalocyanine pigment (β-form) |
| 6.0 | IRGALITE 1300 (Ciba) | Fotoinitiator (IRGACURE 369 + IRGACURE 651 benzildimethylketal) |
| 106.0 | Total formulation | |

0.2 g of a TMPTA solution containing 2.5 wt-% stabilizer were added to 5.0 g of the blue offset ink and were distributed homogeneously in a muller. The inks were printed with a Prüfbau multipurpose printability tester on white Lumiart paper (1.5 g/m$^2$) and were exposed to the radiation of one medium-pressure mercury lamp, at 150 W/cm in an UV curing unit from IST-Metz. The through cure (line speed in m/min) and the surface cure (y/n) of the ink were assessed after the exposure.

The results are as follows:

| Stabilizer | Line speed for through curing of blue offset ink [m/min] |
|---|---|
| 0.1% stabilizer A | 90 |
| 0.1% Stabilizer B | 120 |
| 0.1% Eutectic Blend A/B = 1/9 Mol/Mol, 0.5% solution | 110 |

Yellowing Formulation

| [g] | Product | Description |
|---|---|---|
| 30 | EBECRYL 605 | Standard bisphenol A epoxy acrylate diluted in 25% TPGDA, UCB |
| 10 | EBECRYL 7100 | Amine modified acrylate |
| 5 | EBECRYL 40 | Polyether tetraacrylate, UCB |
| 30 | OTA 480 | Oligomer triacrylate - glycerol derivate, UCB |
| 24 | TPGDA | Tripropylene glycol diacrylate |
| 0.5 | EBECRYL 1360 | Siliconhexaacrylat, UCB |
| 0.5 | DOW CORNING 57 | Silicon-glycol-copolymer, Dow Corning |
| 100.0 | Formulation | |

| | |
|---|---|
| Photoinitiator: | 8% IRGACURE 184 |
| Substrates: | White coil coat plate |
| Application: | for yellowing, Box bar 100 um, Wire bar 6 um |
| Curing: | Hg 2 × 120 Watt/cm (IST) 10 m/min |
| Properties tested: | |
| Yellowing | immediately after 16 h post curing with TLK 40/05 (fluorescent lamp) |
| $L^*a^*b^*$ | measured with CGREC Version 2.61.05 |
| Yi | calculation Formula: $(100*(0.72 \times a^* + 1.79 \times b^*)/L^*)$ |

-continued

| | Product | % in TMPTA | IS 19/07/04* % Stabilisator in OPV | Layer 100 um b* | Layer 100 um b* after 24 h TLK40/05 | Layer 6 um b* |
|---|---|---|---|---|---|---|
| 1 | A | 2.5 | 0.5 | 0.2 | 0.1 | −0.4 |
| | | | 0.1 | −0.1 | −0.3 | −0.4 |
| | | | 0.2 | 0.3 | 0.1 | −0.5 |
| 2 | B | 2.5 | 0.5 | 0.4 | 0.2 | −0.4 |
| | | | 0.1 | 0.5 | 0.3 | −0.4 |
| | | | 0.2 | 1.3 | 1.2 | −0.3 |
| 3 | Eutektic Blend A/B = 1/9 | 2.5 | 0.5 | 0.8 | 0.7 | −0.3 |
| | | | 0.1 | 1.7 | 1.6 | −0.3 |
| | | | 0.2 | 2.2 | 2.1 | −0.2 |

*0.1% correspond 4% of the 2.5% solution of the products in TMPTA

The eutectic blend shows a higher stabilization effect like the commercial Irgastab UV10 (product A) and Product B in particular in the TMPTA/IRGACURE 369 blend. They have no or only a small negative influence on the curing efficiency of the blue offset ink.

The invention claimed is:

1. A radiation curable coating- or ink composition comprising
    a) a photoinitiator;
    b) an eutectic blend of 4-benzylidene-2,6-di-tert-butyl-cyclohexa-2,5-dienone and bis(1-oxy-2,2,6,6-tetramethylpiperidin-4-yl) sebacate.

2. A composition according to claim 1, wherein the coating composition is a pigmented or unpigmented urethane resin, acrylic resin, polyester resin, or epoxy resin.

3. A composition according to claim 1, wherein the ink composition is an offset ink, a flexographic ink, a screen ink or an ink jet ink.

4. A method for increasing the storage stability of a radiation curable coating- or ink composition by adding to the coating or the ink composition, optionally comprising a photoinitiator, a stabilizer blend comprising an eutectic blend of 4-benzylidene-2,6-di-tert-butyl-cyclohexa-2,5-dienone and bis(1-oxy-2,2,6,6-tetramethylpiperidin-4-yl) sebacate.

* * * * *